United States Patent [19]

Theriot et al.

[11] Patent Number: 5,650,548

[45] Date of Patent: Jul. 22, 1997

[54] OLEFIN OLIGOMERIZATION PROCESS

[75] Inventors: Kevin J. Theriot, Baton Rouge; Robert G. Irwin, Prairieville, both of La.

[73] Assignee: Amoco Corporation, Chicago, Ill.

[21] Appl. No.: 491,459

[22] Filed: Jun. 16, 1995

[51] Int. Cl.[6] ..................................................... C07C 2/08
[52] U.S. Cl. ........................... 585/525; 585/500; 585/510; 585/515; 585/520; 585/526; 585/529
[58] Field of Search ................................. 585/500, 510, 585/515, 520, 525, 526, 529

[56] References Cited

U.S. PATENT DOCUMENTS

| | | |
|---|---|---|
| 2,500,161 | 3/1950 | Seger et al. |
| 2,500,163 | 3/1950 | Garwood. |
| 2,766,312 | 10/1956 | Serniuk. |
| 2,806,072 | 9/1957 | Cohen et al. |
| 3,382,291 | 5/1968 | Brennan. |
| 3,769,363 | 10/1973 | Brennan. |
| 3,997,621 | 12/1976 | Brennan. |
| 4,024,203 | 5/1977 | Torck et al. ............... 585/514 |
| 4,172,855 | 10/1979 | Shubkin et al. ............ 585/16 |
| 4,218,330 | 8/1980 | Shubkin ................... 252/46.6 |
| 4,409,415 | 10/1983 | Morganson et al. ........ 585/525 |
| 4,436,947 | 3/1984 | Morganson et al. ........ 585/525 |
| 4,902,846 | 2/1990 | DiLeo et al. ............... 585/525 |
| 4,935,570 | 6/1990 | Nelson et al. .............. 585/329 |
| 4,950,822 | 8/1990 | Dileo et al. ............... 585/310 |
| 4,956,512 | 9/1990 | Nissfolk et al. ........... 585/521 |
| 4,973,789 | 11/1990 | Karn et al. ................ 585/525 |
| 4,982,026 | 1/1991 | Karn et al. ................ 585/18 |
| 5,068,487 | 11/1991 | Theriot .................... 585/510 |
| 5,191,140 | 3/1993 | Akatsu et al. ............. 585/525 |
| 5,225,588 | 7/1993 | Senaratne et al. ........... 560/71 |
| 5,241,085 | 8/1993 | Senaratne et al. ......... 549/396 |
| 5,250,750 | 10/1993 | Shubkin et al. ......... 174/17 LF |
| 5,396,013 | 3/1995 | Theriot .................... 585/510 |
| 5,420,373 | 5/1995 | Hope et al. ............... 585/525 |

*Primary Examiner*—Glenn A. Caldarola
*Assistant Examiner*—Elizabeth D. Wood
*Attorney, Agent, or Firm*—Joseph DiSalvo; Stephen L. Hensley

[57] ABSTRACT

Alpha-olefin oligomer is prepared by contacting an alpha-olefin monomer which contains from about 6 to about 20 carbon atoms with a catalyst system comprising boron trifluoride, a protic promoter, and an organic sulfone, sulfoxide, carbonate, thiocarbonate, or sulfonate. Oligomer containing as much as 50% or more of dimer can be produced at high conversions, at modest reaction temperatures, and in acceptably short reaction periods.

35 Claims, No Drawings

OLEFIN OLIGOMERIZATION PROCESS

TECHNICAL FIELD

This invention relates generally to the preparation of alpha-olefin oligomers which are useful as synthetic lubricants and functional fluids. More particularly, this invention relates to $BF_3$-promoter catalyst systems which use a modifier to control the oligomer product distribution and provide higher percentages of lower oligomers, especially dimers.

BACKGROUND

Alpha-olefin oligomers and their use as synthetic lubricants are well-known. The oligomers are usually hydrogenated in order to improve their stability. Early reports of such oligomeric synthetic lubricants appear in Seger et al. U.S. Pat. Nos. 2,500,161 and Garwood 2,500,163.

Oligomerization of alpha-olefins in a Group IV metal oxide bed using a $BF_3$-protic promoter catalyst is described in U.S. Pat. No. 2,766,312. Promoters referred to therein include water, carboxylic acid, alkyl halides, alcohols and ethers.

U.S. Pat. No. 2,806,072 discloses the dimerization of $C_6$–$C_{12}$ polypropylenes using a preformed $BF_3$-dialkyl ether catalyst.

Oligomerization of olefins using $BF_3$-promoter catalyst complexes of acid anhydrides, esters, ketones and aldehydes is described in U.S. Pat. No. 3,382,291.

U.S. Pat. No. 3,769,363 to Brennan discloses oligomerization of $C_6$–$C_{12}$ normal alpha-olefins, such as 1-decene, with $BF_3$ and $C_5$ carboxylic acid to improve trimer yields.

U.S. Pat. No. 3,997,621 also to Brennan describes oligomerization of $C_6$–$C_{12}$ normal alpha-olefins with $BF_3$ using alcohols or water promoters in conjunction with small amounts of methyl and ethyl esters of a $C_2$–$C_5$ monocarboxylic acid to improve trimer yields.

In U.S. Pat. No. 4,172,855 $BF_3$-promoter catalysts for grafting a second alpha-olefin onto a $C_6$–$C_{12}$ alpha-olefin dimer to form a low volatility lubricating oil is described. The promoters include glycol ethers such as ethylene glycol monomethyl ether and propylene glycol monoethyl ether, and diisobutyl ether.

U.S. Pat. No. 4,218,330 to Shubkin describes dimerization of $C_{12}$–$C_{18}$ alpha-olefin monomer with a $BF_3$-water complex and an excess of $BF_3$. Unreacted monomer is distilled from the reaction product leaving mainly dimer with minor amounts of trimer and higher oligomers. The product is hydrogenated for use as a lubricant.

U.S. Pat. No. 4,436,947 to Morganson et al. discloses oligomerization of $C_6$–$C_{20}$ olefins, such as 1-decene, with $BF_3$ and a mixture of an aliphatic alcohol, an aliphatic ketone, and a polyol. The product is mainly trimer.

U.S. Pat. No. 4,982,026 to Karn describes polymerization of $C_2$–$C_6$ alkene monomers with $BF_3$ and a strong acid, such as phosphoric acid to produce a polymer having a molecular weight of from 250 to 500 and having a high vinylidene content.

U.S. Pat. No. 5,068,487 describes a process for producing products containing predominately dimers and trimers of alpha-olefins using a $BF_3$ catalyst promoted by an alcohol alkoxylate.

U.S. Pat. No. 5,191,140 discloses a process for making alpha-olefin oligomers by use of $BF_3$ promoted by at least two of water, alcohols and anhydrides to peak the reaction at lower molecular weight product.

In U.S. Pat. No. 5,396,013 it is shown that polyethers will moderate promoted $BF_3$-catalyzed oligomerizations to provide either predominately dimer- or trimer-containing oligomers.

U.S. Pat. No. 5,420,373 discloses a process for producing predominately dimer and trimer from $C_6$–$C_{20}$ olefins, such as 1-decene, with $BF_3$ and a hydroxy carbonyl promoter—i.e., a hydroxy ketone or a hydroxy aldehyde. Secondary promoters may also be used, namely aldehydes, alcohols, alcohol alkoxylates, carboxylic acids, ethers, ketones, and their mixtures.

The particular application for which the oligomer oils are used depends largely upon their viscosity, with viscosities of about 2–10 cSt at 100° C. being preferred for general lubricating oil applications. These materials are, in general, mixtures of different percentages of dimer, trimer, tetramer, pentamer and, in the case of the higher viscosity products in this range, higher oligomers as well. To increase viscosity, processes are used which either produce more of the higher oligomers or some of the lower oligomers are removed such as by distillation.

Most lower viscosity dimer products are obtained as by-products of the production of higher viscosity synthetic oils. Because of increasing use of dimers in applications such as low temperature lubricants and drilling fluids, methods for their preferential production are of particular interest. Although higher oligomerization temperatures tend to increase dimer formation, use of such higher temperatures can cause corrosion of process equipment.

SUMMARY OF THE INVENTION

New, highly effective modifiers for $BF_3$-catalyzed oligomerization reactions have been discovered. By the practice of preferred embodiments of this invention it has been found possible to modify the promoted catalytic reaction so that product containing as much as 50% or more of dimer can be produced at high conversions, at modest reaction temperatures, and in acceptably short reaction periods.

The modifiers employed pursuant to this invention are organic sulfones, sulfoxides, carbonates, thiocarbonates, and sulfonates.

Accordingly, in one of its embodiments this invention provides a process of preparing alpha-olefin oligomer which comprises contacting an alpha-olefin monomer which contains from about 6 to about 20 carbon atoms with a catalyst system comprising boron trifluoride, a protic promoter, and an organic sulfone, sulfoxide, carbonate, thiocarbonate, or sulfonate.

In a preferred embodiment the foregoing process is conducted under oligomerization conditions forming a reaction mixture that contains 50 wt. % or more of dimer, terminating the oligomerization in said reaction mixture, and recovering the dimer from said reaction mixture, for example, by distillation. The preferred oligomerization conditions which form 50 wt. % or more dimer are temperatures of about 30° to about 150° C. under an atmosphere comprising boron trifluoride at a pressure of about 5 to about 100 psig, and in proportions in the range of about 0.5 to about 2.0 moles of modifier per mole of promoter. It has been found possible to conduct the process whereby at conversions upwards from 75%, and even above 90%, oligomerization reaction product mixtures containing less than 5 wt. % of tetramer and higher oligomer are formed, and this constitutes a particularly preferred embodiment of this invention. The especially preferred oligomerization conditions which yield 75% and even above 90% conversion and less than 5 wt. % tetramer and higher oligomer are use of 1-decene as the olefin monomer, temperatures of about 40° to about 60° C. under an atmosphere comprising boron trifluoride at a pressure of about 5 to about 100 psig, in proportions of about 1.0 mole % protic promoter based on olefin monomer, and in proportions in the range of about 0.75 to about 1.25 moles of modifier per mole of promoter.

Another preferred embodiment utilizes water and/or at least one alkanol as the catalyst promoter in the each of the foregoing processes.

Still another preferred embodiment involves conducting a process of this invention using as the protic promoter an alcohol alkoxylate such as described in U.S. Pat. No. 5,068,487, such as 1-methoxy-2-propanol and/or 2-methoxyethanol.

A further embodiment of this invention involves use of a modifier of this invention in the form of an oligomer or polymer of sufficient molecular weight to enable the modifier to be readily removed from the reaction product mixture on completion of the oligomerization reaction.

The above and other embodiments and features of this invention will become still further apparent from the ensuing description and appended claims.

FURTHER DESCRIPTION

The olefins used in making the oligomers are predominately (at least 50 mole %) $C_6$–$C_{20}$ straight chain (i.e., linear) monoolefinically unsaturated hydrocarbons in which the olefinic unsaturation exists in the 1- or alpha-position of the straight chain. Such alpha-olefins are available as articles of commerce, and can be made by thermal cracking of paraffinic hydrocarbons or by well-known Ziegler ethylene chain growth technology. Individual olefins can be used as well as mixtures of such olefins. Examples of olefins that can be used are 1-hexene, 1-heptene, 1-octene, 1-nonene, 1-decene, 1-undecene, 1-dodecene, 1-tridecene, 1-tetradecene, 1-hexadecene, 1-octadecene, 1-eicosene, and mixtures of two or more of such 1-olefins. Remotely branched 1-olefins such as 5-methyl-1-heptene, 6-methyl-1-heptene, 6-methyl-1-octene, 7-methyl-1-octene, 6,7-dimethyl-1-octene, 7,7-dimethyl-1-octene, 8-methyl-1-nonene, and like 1-olefins can also be used especially when used together with linear 1-olefins. The more preferred olefins are linear alpha-olefin monomers containing about 8–14 carbon atoms. The most preferred 1-olefin monomer is 1-decene.

Minor amounts of up to about 50, and usually less than 25 mole of internal and/or vinylidene olefins can be present in the olefin monomers.

Oligomerization is effected by contacting the monomer(s) with a catalytic amount of boron trifluoride, which typically is at least about 0.002 moles per mole of olefin, together with a protic promoter and a modifier. Preferably the reaction is performed in a reaction mixture saturated with boron trifluoride or in a sealed agitated reactor under an atmosphere enriched in boron trifluoride.

Among the protic promoters that can be used are water, carboxylic acids, mineral acids, alcohols, phenols, carboxylic acid esters and anhydrides, ketones, aldehydes, hydroxy ketones, hydroxy aldehydes, alcohol alkoxylates, and mixtures of any two or more of the foregoing. Preferred are water, $C_1$ to $C_{24}$ alcohols and, more preferably, $C_1$ to $C_{12}$ alcohols, and alcohol alkoxylates such as described in U.S. Pat. No. 5,068,487. Examples of preferred alcohols include methanol, ethanol, 1-propanol, 2-propanol, 1-butanol, 2-methyl-1-propanol, 1-pentanol, 2-pentanol, 1-hexanol, 2-hexanol, 1-heptanol, 1-octanol, 2-ethyl-1-hexanol, 1-nonanol, 1-decanol, 1-undecanol, 1-dodecanol, and mixtures of two or more $C_1$ to $C_{12}$ alcohols. Of these, 1-propanol and 1-butanol are particularly preferred. Examples of alcohol alkoxylates include 2-methoxyethanol, 2-ethoxyethanol, 1-methoxy-2-propanol, 4-ethoxy-1-butanol, 2-butoxyethanol, and their analogs and homologs. The protic promoter is used in an oligomerization-promoting amount, i.e., an amount that causes the $BF_3$ to function as an oligomerization catalyst, such as for example from about 0.001 to about 0.04 moles per mole of alpha-olefin monomer(s). In general the $BF_3$ is used in a molar excess relative to the quantity of promoter(s) used, typically by maintaining a pressurized atmosphere of $BF_3$ or $BF_3$ and nitrogen in the reaction vessel. The promoter can be mixed with the olefin feed or the promoter can be charged separately to the reactor, either entirely at the outset or portionwise as the oligomerization proceeds.

The organic sulfones, sulfoxides, carbonates, thiocarbonates, and sulfonates used in the practice of this invention can either contain no additional functionality in the molecule or they can contain additional functionality provided the functionality is such that it does not significantly impair the effectiveness of the modifier. Linkages or substituents that do not impair the effectiveness of the modifiers and that thus can be present therein are the following: halide, hydrocarbyloxy, hydrocarbylthio, ether oxygen linkage, thioether sulfur linkage, nitro, nitrile, hydrocarbylsilyl, carbonyl, and thiocarbonyl.

A few example of modifiers having additional non-harmful functionality are: 2,4-bis(methylsulfonyl)-1-chlorobenzene; p-chlorophenyl 2-chloro-1,1,2-trifluoroethyl sulfone; 4-chlorophenyl sulfone; 4-chlorophenyl sulfoxide; 4-fluoro-3-nitrophenyl 3-nitrophenyl sulfone; p-fluorophenyl methyl sulfone; p-fluorophenyl phenyl sulfone; p-fluorophenyl p-tolyl sulfone; (phenylsulfonyl) acetonitrile; methyl methylsulfinylmethyl sulfide; 4,4'-sulfonyl-bis(methylbenzoate); 4-nitrophenyl sulfone; phenyl trimethylsilylmethyl sulfone; 4-methoxyphenyl methyl sulfone; 4-acetylphenyl methyl sulfone; ethyl phenacyl sulfone; phenyl phenacyl sulfone; phenyl phenacyl sulfoxide; methyl p-nitrobenzene sulfonate; cyanomethyl benzene sulfonate; methyl methanethio sulfonate; bis(4-nitrophenyl) carbonate; diethyl pyrocarbonate; bis(2-methoxyphenyl) carbonate; lithium trifluoromethane sulfonate; 4-methoxyphenyl benzene sulfonate; methyl fluorobenzene sulfonate; and methyl trifluoromethyl sulfonate.

In general, the preferred modifiers are those that contain no additional functionality in the molecule. In other words, the preferred modifiers are hydrocarbyl sulfones, hydrocarbyl sulfoxides, hydrocarbyl carbonates, hydrocarbyl thiocarbonates and hydrocarbyl sulfonates.

The organic sulfone modifiers can be monosulfones or polysulfones such as disulfones. Preferred hydrocarbyl monosulfone modifiers can be depicted by the formula:

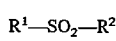

$$R^1-SO_2-R^2$$

where $R^1$ and $R^2$ are, independently, hydrocarbyl groups bonded to the sulfur atom, or taken together constitute a single hydrocarbyl group forming a heterocyclic ring system in which the sulfur atom is singly-bonded to two different carbon atoms of the ring and is thus the hetero atom of the ring system. $R^1$ and $R^2$ can be, independently, aliphatic, cycloaliphatic or aromatic, and when aliphatic or cycloaliphatic, either or both of $R^1$ and $R^2$ can be saturated or olefinically unsaturated. Normally, $R^1$ and $R^2$ will each contain up to about 30 carbon atoms, and more preferably up to about 12 carbon atoms each.

Examples of compounds in which $R^1$ and $R^2$ are separate hydrocarbyl groups include dialkyl sulfones, dialkenyl sulfones, diaryl sulfones, aryl alkyl sulfones, diaralkyl sulfones, and aryl alkenyl sulfones, such as dimethyl sulfone, diethyl sulfone, dipropyl sulfone, dibutyl sulfone, butyl isopropyl sulfone, divinyl sulfone, diphenyl sulfone, phenyl p-tolyl sulfone, methyl phenyl sulfone, ethyl phenyl sulfone, methyl p-tolyl sulfone, dibenzyl sulfone, phenyl vinyl sulfone, and analogous compounds. Mixtures of such sulfones can be used, if desired.

Sulfone modifiers in which $R^1$ and $R^2$ form a heterocyclic ring system with the sulfur atom are cycloparaffinic sulfones or cycloolefinic sulfones, such as for example, sulfolane, 3-methylsulfolane, 2,4-dimethylsulfolane, sulfolene, 2,4-dimethyl-3-sulfolene, dibenzothiophene sulfone, pentamethylene sulfone, and analogous cyclic compounds. Typically, the cyclic sulfones will contain up to about 24 and preferably up to about 18 carbon atoms in the molecule.

Sulfones having more than one sulfone functional group per molecule are exemplified by the disulfones represented by the general formula:

$$R^3\text{—}SO_2\text{—}R\text{—}SO_2\text{—}R^4$$

where $R^3$ and $R^4$ are, independently, hydrocarbyl groups bonded to the sulfur atom, and R is an alkylene or arylene group bonded to both sulfur atoms. Typically $R^3$ and $R^4$, independently, will contain up to about 30 carbon atoms each, and more preferably up to about 12 carbon atoms each, and are aliphatic, cycloaliphatic or aromatic groups. When aliphatic or cycloaliphatic, either or both of $R^3$ and $R^4$ can be saturated or olefinically unsaturated. Typically R will be an alkylene group having up to about 18 carbon atoms (and preferably having up to about 8 carbon atoms) or an arylene group having 6 to about 18 carbon atoms (and preferably having 6 to about 12 carbon atoms). Illustrative examples of such compounds include ethylenebis(phenylsulfone), 1,3-propylenebis(ethylsulfone), 1,4-butylenebis(ethylsulfone), 3,3-bis(ethylsulfonyl)pentane, 1,4-phenylenebis(ethylsulfone), 1,4-phenylenebis(phenylsulfone), and analogous compounds.

Preferred sulfoxide modifiers used pursuant to this invention can be depicted by the formula:

$$R^5\text{—}SO\text{—}R^6$$

where $R^5$ and $R^6$ are, independently, hydrocarbyl groups bonded to the sulfur atom, or taken together constitute a single hydrocarbyl group forming a heterocyclic ring system including the sulfur atom. When separate groups $R^5$ and $R^6$ can be, independently, aliphatic, cycloaliphatic or aromatic, and when aliphatic or cycloaliphatic, either or both of $R^5$ and $R^6$ can be saturated or olefinically unsaturated. Normally, as independent groups $R^5$ and $R^6$ will each contain up to about 30 carbon atoms, and more preferably each will contain up to about 12 carbon atoms. When $R^5$ and $R^6$ are in the form of a single hydrocarbyl group, the cyclic sulfoxide will typically contain up to about 24 and preferably up to about 18 carbon atoms in the molecule. Thus the sulfoxide modifiers include dialkyl sulfoxides, dicycloalkyl sulfoxides, diaryl sulfoxides, diaralkyl sulfoxides, aryl alkyl sulfoxides, aryl alkenyl sulfoxides, cycloaliphatic sulfoxides, and similar compounds of this type. Examples of such sulfoxides include dimethyl sulfoxide, diethyl sulfoxide, dipropyl sulfoxide, dibutyl sulfoxide, diallylsulfoxide, diphenyl sulfoxide, di-p-tolyl sulfoxide, dibenzyl sulfoxide, methyl isopropyl sulfoxide, methyl allyl sulfoxide, tetramethylene sulfoxide, pentamethylene sulfoxide, and their analogs and homologs.

Preferred carbonate and thiocarbonate modifiers can be depicted by the formula:

$$R^7\text{—}QCQ\text{—}R^8 \atop \|\ Q$$

where Q is an oxygen atom or a sulfur atom, and $R^7$ and $R^8$ are, independently, hydrocarbyl groups bonded to the carbonate or thiocarbonate moiety, or taken together constitute a single hydrocarbyl group forming a heterocyclic ring system including the carbonate or thiocarbonate functional group. $R^7$ and $R^8$, when separate groups, can be, independently, aliphatic, cycloaliphatic or aromatic, and when aliphatic or cycloaliphatic, either or both of $R^7$ and $R^8$ can be saturated or olefinically unsaturated. Normally, $R^7$ and $R^8$ as independent groups will each contain up to about 30 carbon atoms, and more preferably will contain up to about 12 carbon atoms each. When in the form of cyclic ring system, $R^7$ and $R^8$ constitute a polymethylene group which can be unsubstituted or substituted on one or more carbon atoms thereof by univalent hydrocarbyl groups such as alkyl, cycloalkyl, aryl, and aralkyl groups of up to about 18 carbon atoms, and more preferably alkyl groups of from 1 to about 12 carbon atoms. Illustrative examples of the carbonate and thiocarbonate modifiers include dimethyl carbonate, diethyl carbonate, dipropyl carbonate, dibutyl carbonate, dipentyl carbonate, ethyl methyl carbonate, diphenyl carbonate, dibutyl carbonate, 5,5-dimethyl-1,3-dioxan-2-one, dibutyl thiocarbonate, diphenyl thiocarbonate, tetramethylene thiocarbonate, 2-methyltetramethylene thiocarbonate, 2,4-dimethyltetramethylene carbonate, and similar carbonates and thiocarbonates. The carbonates are preferred because of their greater availability and lower cost.

The hydrocarbyl sulfonates can be aliphatic, cycloaliphatic or aromatic in character and can be sulfonic acid esters or salts. The sulfonates can have one, or more than one, sulfonic ester or sulfonic acid salt group in the molecule. Generally the sulfonates will contain up to about 60 or more carbon atoms in the molecule. For example, the sulfonates can be derived from alkylaromatic hydrocarbons formed by alkylating benzene, toluene, xylene, etc., with long chain alkenes or polyolefins of suitable molecular weight. The esterifying group can be derived from any suitable alcohol, thiol, phenol or thiophenol. The salts can be inorganic salts or organic salts, such as, for example, lithium, sodium, potassium, calcium, magnesium and barium alkylaryl or alkane sulfonates and pyridinium alkylaryl or alkane sulfonates. Typical esters of hydrocarbyl sulfonic acids include methyl methane sulfonate, phenyl methane sulfonate, butyl ethane sulfonate, methyl 1-decane sulfonate, isopropyl 1-naphthalene sulfonate, dimethyl 2,6-naphthalene sulfonate, ethyl p-toluene sulfonate, butyl benzene sulfonate, 2-ethylhexyl 1-tetradecane sulfonate, methyl 4-biphenyl sulfonate, and analogous compounds. Examples of hydrocarbyl sulfonate salts include lithium octylbenzene sulfonate, sodium 1-decane sulfonate, potassium 1-dodecane sulfonate, pyridinium p-toluene sulfonate, tetraethylammonium p-toluene sulfonate, lithium 1-tridecane sulfonate, calcium octylbenzene sulfonate, and their analogs.

As noted above, olefin functionality may be included in the modifier. In such cases the modifier may become incorporated into the oligomer, and this may be desirable when using the oligomer for certain heavy duty lubrication applications.

One special class of modifiers of this invention is made up of the oligomeric and polymeric forms of the modifiers. These may be formed by appropriate known direct or indirect synthesis procedures, and the oligomers can be formed from one or more than one monomer as long as the overall product contains the requisite functionality (and optionally and additionally, the permissible functionality) of the modifiers of this invention, and does not contain functionality that would impair the ability of the modifier to perform its intended function. The functionality can be included in the oligomer or polymer chain, as in the case, for example, of an oligomeric or polymeric aromatic sulfone. Alternatively, the functionality can be in dependent side chains of the oligomer or polymer. Conceivably, the functionality could be in both the oligomer or polymer chain and in dependent side chains as well. A feature of such oligomeric or polymeric modifiers is that they may be readily separated from the oligomerization product mixture, such as by filtration, or by precipitation and subsequent filtration, centrifugation or decantation.

Methods for forming such oligomeric or polymeric modifiers are known and reported in the literature. For example, methods for synthesis of poly(sulfoxides), poly(sulfones), and appropriate derivatives of poly(sulfonic acids) such as poly(sulfonates), poly(sulfonic acid salts), and poly(sulfonyl halides) are referred to in *Encyclopedia of Polymer Science and Technology*, Volume 13, Interscience Publishers, copyright 1970, pages 460–470 and in the relevant references cited therein in the bibliography on pages 472–477, all of which material is incorporated herein by reference.

While normally a single modifier is used in the process, suitable mixtures of two or more modifiers can be employed, if desired.

In conducting the process of this invention the alpha-olefin or mixture of alpha-olefins, boron trifluoride, protic promoter and modifier can be charged to the reactor in any suitable sequence. Preferably, however, the modifier should be present before any substantial amount of oligomerization has occurred. In this way the maximum beneficial reaction modifying effect of the modifier can be realized.

The reaction can be carried out as a batch, continuous, or semi-continuous process at temperatures which typically are in the range of 0° to 200° C., and preferably in the range of about 30° to about 150° C. More preferably, the temperature is maintained in the range of about 20° to about 60° C., and especially in the range of about 40° to about 60° C. The reaction is typically conducted at pressures ranging from atmospheric up to, for example, 1000 psig, and preferably in the range of about 5 to about 100 psig. The progress of the reaction can be monitored, if desired, by taking samples of the oligomerization mixtures at suitable periods during the course of the reaction and subjecting the sample to gas chromatographic (GC) analysis. In this connection, all references in this specification and in the claims to weight % of oligomer components in the oligomerization reaction product mixture are based on GC area percentages in which the analyses are conducted using a Hewlett Packard 5890 gas chromatograph equipped with a flame ionization detector and a methyl siloxane column operated under the following conditions: initial temperature=100° C.; final temperature=350° C.; Rate=15° C./minute.

The reaction can be conducted in a single stirred reactor or in a series of reactors.

To terminate the oligomerization reaction when the desired product distribution and olefin conversion have been achieved, the dimer enriched reaction mixture can be quenched with or in water or an aqueous solution, such as a solution of a salt or a base, or more preferably a solution of a strong base such as sodium hydroxide or potassium hydroxide. The organic phase is recovered and unless the oligomeric product is to be used in the form produced, the reaction product is distilled to recover the product fraction(s) desired. Unreacted olefin can be recovered and recycled.

In most cases the modifiers are used in proportions relative to the promoter that will peak the oligomerization at the dimer stage, but in some cases the proportions can be adjusted for peaking at the trimer stage. Thus in general the ratio of modifier to promoter will usually fall somewhere within the range of from about 0.1 to about 10 moles of modifier per mole of promoter, and typically within the range of from about 0.5 to about 2 moles of modifier per mole of promoter. For producing product containing at least 50 wt. % in dimer, the preferred proportions fall in the range of from about 0.75 to about 1.25 moles of modifier per mole of promoter. Where the modifier is difunctional (e.g., when a disulfone is used) the molar amount of the modifier should be reduced by about one-half, and further proportionate reductions should be considered for use when the modifier being used is in the form of an oligomer or polymer. It should be understood that one should use a suitable ratio for achieving the particular results desired under the particular reaction conditions and with the particular materials selected for use. Thus the ratio that will best serve the needs of the situation at hand can be determined by performing a few oligomerizations using procedures such as given in the following illustrative examples.

EXAMPLES

1-Decene, 1-butanol (1.0 mole % based on 1-decene) and the amount of the modifier (see in Table I), are charged to a reactor equipped with cooling means, stirring means and inlet/outlet ports. The reactor is sealed and pressurized (10 psig) with boron trifluoride, and the temperature of the stirred mixture is maintained at 50° C. by external cooling for the duration of the reaction. Periodic samples are taken for GC analysis to monitor the progress of the reaction. To terminate the reaction, the reactor is vented into a caustic scrubber, purged with nitrogen, and the reactor contents are drained into 10% aqueous caustic solution. The product is then washed twice with water. The final product mixture is analyzed by GC for product composition.

In Table I the modifiers are identified as follows: A is dimethyl sulfoxide, B is propylene carbonate and C is sulfolane. Control 1 of Table I was a run carried out in the same manner as the above examples except that no modifier was used. In Control 2 of Table I the modifier, in this case, propylene carbonate, was used without the protic promoter, and the temperature was 45° C.

Table II shows the results of another Example of this invention which was conducted as in Example 5 except that 1.0 mole % of 1-methoxy-2-propanol was used as the protic promoter.

TABLE I

| Example | Promoter | Modifier (mole %) | Time, min. | $C_{20}$, % | $C_{30}$, % | $C_{40}$, % | $C_{50}$, % | Conversion, % |
|---|---|---|---|---|---|---|---|---|
| 1 | Yes | A (1.0) | 180 | 58.3 | 16.5 | 2.3 | 0.3 | 77.5 |
| 2 | Yes | A (0.5) | 150 | 47.0 | 24.8 | 3.0 | 0.5 | 75.3 |
| 3 | Yes | A (1.5) | 180 | 37.7 | 9.7 | 0.7 | — | 48.2 |
| 4 | Yes | B (1.0) | 180 | 67.1 | 21.6 | 3.6 | 0.1 | 92.4 |
| 5 | Yes | C (1.0) | 180 | 74.3 | 15.2 | 1.5 | — | 91.0 |
| Control 1 | Yes | None | 120 | 11.8 | 65.2 | 16.7 | 3.8 | 97.6 |
| Control 2 | No | B (1.0) | 120 | 6.2 | 1.8 | — | — | 7.5 |

TABLE II

| Example | Promoter | Modifier (mole %) | Time, min. | $C_{20}$, % | $C_{30}$, % | $C_{40}$, % | $C_{50}$, % | Conversion, % |
|---|---|---|---|---|---|---|---|---|
| 6 | Yes | C (1.0) | 180 | 80.3 | 10.9 | 1.0 | 0.6 | 92.8 |

It will be noted from the results of Control 2 that the modifier is not itself a promoter as no significant oligomerization occurred. Thus the modifier cooperates with the boron trifluoride catalyst and the protic promoter to provide the desired peaking or enrichment of the reaction product at the dimer stage.

The entire disclosure of each and every U.S. patent referred to in any portion of this specification is incorporated herein by reference for all purposes.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process of preparing alpha-olefin oligomer which comprises contacting an oligomerizable olefin monomer with a catalyst system comprising a catalytic amount of boron trifluoride, an oligomerization promoting amount of a protic promoter, and an organic modifier selected from the group consisting of sulfoxide, carbonate, and sulfonate at a pressure from about atmospheric to about 1000 psig, a temperature of about 0° C. to about 200° C., and a molar ratio in the range of about 0.1 moles to about 10 moles of modifier per mole of promoter wherein the olefin monomer is a $C_6$ to $C_{20}$ linear olefin comprising at least 50 mole % alpha olefin.

2. The process according to claim 1 wherein the protic promoter is selected from the group consisting of water, at least one alcohol, and mixtures thereof.

3. A process according to claim 1 wherein the protic promoter is an alcohol.

4. A process according to claim 1 wherein the olefin monomer has from 8 to 14 carbon atoms.

5. A process according to claim 1 wherein the olefin monomer is 1-decene.

6. A process according to claim 1 wherein the modifier is a hydrocarbyl sulfoxide.

7. A process according to claim 1 wherein the modifier is a hydrocarbyl carbonate.

8. A process according to claim 1 wherein the modifier is a hydrocarbyl sulfonate.

9. A process according to claim 1 wherein the temperature is maintained in the range of about 20° to about 60° C. and wherein the pressure is maintained in the range of about 5 to about 100 psig.

10. A process according to claim 1 wherein the modifier is selected from the group consisting of dimethylsulfoxide and propylene carbonate.

11. A process of preparing alpha-olefin oligomer which comprises contacting an oligomerizable olefin monomer wherein the olefin monomer is $C_8$ to $C_{14}$ linear olefin comprising at least 50 mole % alpha olefin with a catalytic amount of boron trifluoride, a protic promoter, and a modifier selected from the group consisting of organic sulfoxides, organic carbonates, and organic sulfonates, at a temperature in the range of about 30° to about 150° C., under an atmosphere comprising boron trifluoride at a pressure in the range of 5 psig to about 100 psig, and in proportions in the range of about 0.5 to about 2 moles of modifier per mole of promoter thereby forming an oligomerization product mixture containing 50 wt. % or more of dimer.

12. A process according to claim 11 wherein the protic promoter is selected from the group consisting of water, at least one alcohol, and mixtures thereof.

13. A process according to claim 11 wherein the olefin monomer is 1-decene.

14. A process according to claim 11 wherein the oligomerization is terminated by quenching the said oligomerization product mixture with water or an aqueous solution.

15. A process according to claim 11 wherein said proportions are in the range of about 0.75 to about 1.25 moles of modifier per mole of promoter.

16. A process according to claim 11 wherein the temperature is maintained in the range of about 20° to about 60° C.

17. A process according to claim 11 wherein the olefin monomer is 1-decene, and wherein said proportions are in the range of about 0.75 to about 1.25 moles of modifier per mole of promoter.

18. A process according to claim 11 wherein the protic promoter is at least one alcohol and wherein the modifier is selected from the group consisting of a hydrocarbyl sulfoxide, a hydrocarbyl carbonate, and a hydrocarbyl sulfonate.

19. A process according to claim 18 wherein the olefin monomer is 1-decene, and wherein said promoter and said modifier are employed in equimolar proportions.

20. A process according to claim 11 wherein the protic promoter is at least one alcohol, wherein the modifier is selected from the group consisting of dimethylsulfoxide and propylene carbonate, and wherein the temperature is maintained in the range of about 40° to about 60° C.

21. A process according to claim 20 wherein said promoter and said modifier are employed in equimolar proportions.

22. A process according to claim 21 wherein the olefin monomer is 1-decene.

23. A process according to claim 22 wherein the protic promoter is selected from the group consisting of 1-propanol, 1-butanol, 1-methoxy-2-propanol, and 2-methoxyethanol.

24. A process according to claim 1 wherein the modifier is an organic thiocarbonate.

25. A process according to claim 1 wherein the modifier is a hydrocarbyl thiocarbonate.

26. A process according to claim 2 in which the alcohol is an alcohol alkoxylate.

27. A process according to claim 3 in which the alcohol is an alcohol alkoxylate.

28. A process according to claim 12 in which the alcohol is an alcohol alkoxylate.

29. A process according to claim 18 wherein the modifier is a hydrocarbyl thiocarbonate.

30. A process according to claim 20 in which the alcohol is an alcohol alkoxylate.

31. A process of preparing alpha-olefin oligomer which comprises contacting an oligomerizable olefin monomer with a catalyst system consisting of a catalytic amount of boron trifluoride, an oligomerization promoting amount of a protic promoter, and an organic sulfone modifier under an atmosphere comprising boron trifluoride at a pressure from about atmospheric to about 1000 psig, a temperature of about 0° C. to about 200° C., and a molar ratio in the range of about 0.1 mole to about 10 moles of organic sulfone modifier per mole of promoter wherein the olefin monomer is a $C_6$ to $C_{20}$ linear olefin comprising at least 50 mole % alpha olefin.

32. A process according to claim 31 wherein the organic sulfone modifier is sulfolane.

33. A process of preparing alpha-olefin oligomer which comprises contacting an oligomerizable olefin monomer, wherein the olefin monomer is $C_8$ to $C_{14}$ linear olefin comprising at least 50 mole % alpha olefin, with a catalyst system consisting of a catalytic amount of boron trifluoride, a protic promoter employed in the range of about 1.0 mole % based on olefin monomer, and an organic sulfone modifier at a temperature in the range of about 30° to about 150° C., under an atmosphere comprising boron trifluoride at a pressure in the range of 5 psig to about 100 psig, and in proportions in the range of about 0.5 to about 2 moles of organic sulfone modifier per mole of promoter thereby forming an oligomerization product mixture containing at least 50 wt. % dimer.

34. A process according to claim 33 wherein the organic sulfone modifier is a hydrocarbyl monosulfone.

35. A process according to claim 33 wherein the organic sulfone modifier sulfolane.

* * * * *

UNITED STATES PATENT AND TRADEMARK OFFICE
CERTIFICATE OF CORRECTION

PATENT NO. : 5,650,548
DATED : July 22, 1997
INVENTOR(S) : Kevin J. Theriot, Robert G. Irwin It is certified that error appears in the above-identified patent and that said Letters Patent is hereby corrected as shown below:

| Col. | Line | |
|---|---|---|
| 3 | 48-49 | "25 mole of internal and/or vinylidene olefins" should read --25 mole % of internal and/or vinylidene olefins-- |
| 8 | 22-23 | "at least 50 wt. % in dimer," should read --at least 50 wt. % dimer,-- |
| 12 | 24-25 | "wherein the organic sulfone modifier sulfolane." should read --wherein the organic sulfone modifier is sulfolane.-- |

Signed and Sealed this

Fifteenth Day of December, 1998

BRUCE LEHMAN

*Attest:*

*Attesting Officer*

*Commissioner of Patents and Trademarks*